United States Patent [19]

Anthony et al.

[11] Patent Number: 5,125,279
[45] Date of Patent: Jun. 30, 1992

[54] SYSTEM FOR ANALYZYING COTTON

[75] Inventors: William S. Anthony, Greenville; Oliver L. McCaskill, Leland, both of Miss.

[73] Assignee: The United States of America as represented by the Secretary of the Agriculture, Washington, D.C.

[21] Appl. No.: 447,352

[22] Filed: Dec. 7, 1989

[51] Int. Cl.⁵ .................................. G01N 1/20
[52] U.S. Cl. ................................ 73/866
[58] Field of Search .............. 73/866, 863, 863.01, 73/863.41, 863.51, 863.54, 863.71, 864.81, 160; 250/341, 358.1, 359.1, 360.1; 356/36, 237, 245; 19/105, 97.5, 150, 157, 296, 161.1; 100/99

[56] References Cited

U.S. PATENT DOCUMENTS

| | | | |
|---|---|---|---|
| 3,005,152 | 10/1961 | Jennings, Jr. et al. | 100/99 |
| 3,005,153 | 10/1961 | Berkley et al. | 100/99 |
| 3,611,673 | 10/1971 | Carkhuff | 100/99 |
| 3,869,213 | 3/1975 | Greene | 356/244 |
| 3,869,910 | 3/1975 | Scaletta | 356/244 |
| 3,999,860 | 12/1976 | Demsky et al. | 356/402 |
| 4,400,850 | 8/1983 | Burnett | 19/105 |
| 4,649,753 | 3/1987 | Goodsmith | 73/865.8 |

FOREIGN PATENT DOCUMENTS

| | | | |
|---|---|---|---|
| 0174738 | 10/1984 | Japan | 250/341 |
| 8911090 | 11/1989 | PCT Int'l Appl. | |
| 1310723 | 5/1987 | U.S.S.R. | 356/245 |

Primary Examiner—Robert Raevis
Attorney, Agent, or Firm—M. Howard Silverstein; John D. Fado

[57] ABSTRACT

A system for continuously analyzing cotton moving through a chute in a processing plant comprising cyclically displacing a small mass of cotton from its pathway through the chute toward one of the side walls, and pressing the mass against such side wall so that the mass presents a face of uniform cotton density on that part of the mass which is pressed against the side wall, so that the mass may be accurately analyzed for properties such as color, trash content, and/or moisture content; and removing pressure from the mass after analysis, to permit it to resume its movement through the chute.

31 Claims, 2 Drawing Sheets

SYSTEM FOR ANALYZYING COTTON

Field

The present invention relates to analyzing cotton as it is being processed.

Prior Art

Presently there is no known system for continuously analyzing cotton for color, trash or moisture content as it is being processed.

Summary

We now have developed such a system. Generally, the invention comprises moving bulk cotton (e.g., seed cotton or lint cotton) through a zone partly defined by two opposing surfaces, in a pathway generally parallel to such surfaces, displacing a mass of cotton from the pathway toward a first of said two surfaces, away from the second of said surfaces, while permitting part of the cotton moving through the zone to pass therethrough without displacement; and pressing the displaced mass against such first surface so that the mass presents a face of uniform cotton density on that part of the mass which is pressed on such surface; wherein said uniform density is sufficient to enable the mass to be accurately analyzed by means such as optical or infrared scanners for at least one of the following properties: color, trash content, moisture content.

Ordinarily, the system is carried out in an intermittent or cyclic manner, so that a different mass of cotton, but a mass of essentially the same density each time, is pressed against the surface at time intervals; and, after compression, the pressure is removed, and each mass is allowed to resume its pathway through the zone, parallel to the opposing surfaces.

As used in the specification and claims, the phrase, "a face of uniform cotton density", in reference to the mass of cotton being pressed against an interior surface of the zone, means that the face of the mass which is pressed against the surface essentially is filled with cotton and impurities, with no voids. In other words, the mass is sufficiently compressed so that its flattened face essentially is completely occupied by cotton and impurities. This enables an optical or other analyzer adjacent the flattened face to make an analysis thereof, through, for example, a lens or window, which measurement is an accurate reflection of such properties of the mass as color, trash content, and moisture content.

The zone defined by the two surfaces ordinarily is a holding zone or chute in a cotton ginning system through which the cotton slowly is moving in a downward direction. The analyzer may be incorporated into the first holding chute in the ginning system that is located immediately prior to drying and precleaning treatment, which chute is known in the art as part of the "feed control." Other holding zones in the gin, such as the holding chute immediately above the extractor-feeder, or the tramper box of a bale packaging system, may be adapted to incorporate the analyzing system of the present invention. The system also may be employed in the feed hopper of a textile mill.

The present invention allows the cotton to be compressed pneumatically or hydraulically while slowly moving through a "feed control" holding chute, so as to present a face of uniform cotton density to an analyzing device.

An object of the present invention is to provide uniform cotton density on a face of the cotton mass to enable immediate and increased accuracy of analysis to be performed thereon, including color (e.g., yellowness and grayness), trash content (e.g., area and number of trash particles), leaf grade, and moisture content.

Another object is to intermittently or cyclically press different cotton masses against the analyzer during slow passage of bulk cotton through a holding zone thereby enabling analysis to be carried out without removing samples from the system.

A further object is to provide analysis data that may be employed to automatically or manually adjust machine variables, so as to improve the final product.

A still further object is to provide portable and easily adapatable analysis equipment for any gin configuration.

Yet another object of the present invention is to provide uniform samples for grading.

An even further object is to provide color grade, trash grade, and moisture of cotton continuously as it is processed at a gin.

Even yet further, an object is to provide a mass of cotton of essentially the same density each time a mass is compressed, so as to provide a constant density of cotton for analysis at an adjacent or remote location.

An even still further object is to provide an apparatus for analyzing flowable solids other than clumps of cotton, such as flowable particulate material, including seeds, man-made fibers, pharmaceuticals, coal, and so forth, that are flowing through a zone, but are not necessarily compressible; wherein small samples of the flowing material intermittently are pressed against an analyzer in the zone to be analyzed for properties such as size, impurities, shape, color, moisture. Depending upon the size of the particulates, the material does not necessarily essentially fill up the analysis window, with no voids, in the manner of compressible bulk cotton.

Other objects and advantages will be obvious from the following more detailed description of the invention in which.

Detailed Description

Figure 1:
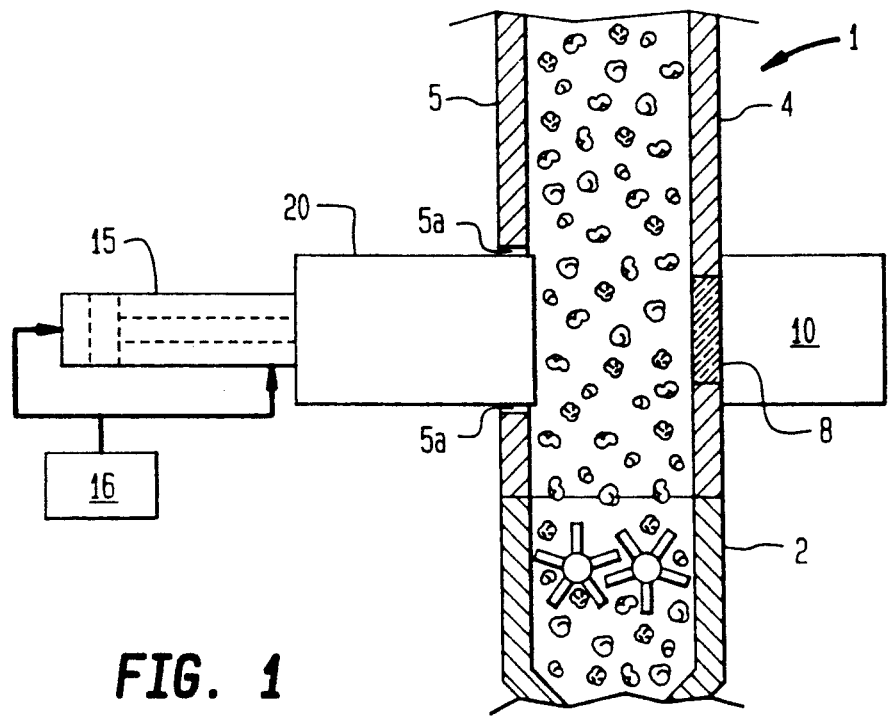
FIG. 1 illustrates the basic elements of the invention.

In FIG. 1, reference numeral 1 designates a typical holding chute or hopper in a ginning system, wherein the chute passes bulk cotton to, for example, the feeding element 2. The cotton moves downward through the chute, usually at a speed of a few feet per minute, typically 3–5 feed per minute. Chute dimensions, in the case of a "feed control" holding chute, typically are 4–16 feet high, 4–12 feet wide, 1–4 feet deep. Other holding chutes, e.g., the hopper for an extractor-feeder, may have the following dimensions: 1–4 feet high, 4–12 feet wide, 1–3 feet deep.

Reference numerals 4 and 5 designate first and second opposing walls or surfaces, preferably the front and back walls of the chute, wherein the distance therebetween may be about 1–4 feet, typically about 2 feet, in the case of a feed control holding chute. Wall 4 includes a window or lens 8. Behind the window is an analyzing means schematically illustrated by reference numeral 10.

One or more conventional analyzing instruments may be employed as the analyzing means. Typically, the analyzing means employs electromagnetic energy (e.g., light, infrared) to detect properties of the seed cotton, such as color, trash content and moisture content. Window or lens 8 is transparent to the extent to permit entry and reflection of electromagnetic rays of the analyzing devices. In lieu of inserting a window in wall 4, the analyzing instrument itself, i.e., the lens portion thereof, may be inserted into an opening in the wall.

If two different analyzers are employed in a side-by-side manner, then two side-by-side windows or openings may be provided in wall 4, as opposed to one large window. The size of the cotton mass being compressed or compacted thereagainst should be large enough to cover the single large window, or both of the side-by-side windows.

Conventional analyzers known in the cotton analysis art may be employed in the practice of the present invention, and include video cameras for trash content analysis, as exemplified by the "Color/Trash Meter" made by Motion Control, Inc., and a similar device by Spinlab, Inc.; and infrared moisture sensors by Infrared Engineering, Inc. or Moisture Systems Corporation. These instruments previously have been employed to analyze cotton samples, remote from the cotton processing point; and sometimes the sample is compressed at the remote analyzer.

Adjacent to wall 5 at opening 5a, directly opposite window 8, is a conventional piston-cylinder assembly illustrated by reference numeral 15 fixed to a frame member (not shown), supplied with fluid pressure from a source 16. The assembly is connected to a ram 20 that intermittently or cyclically displaces cotton from its downward pathway and compresses the displaced cotton against the window 8.

Figure 2:
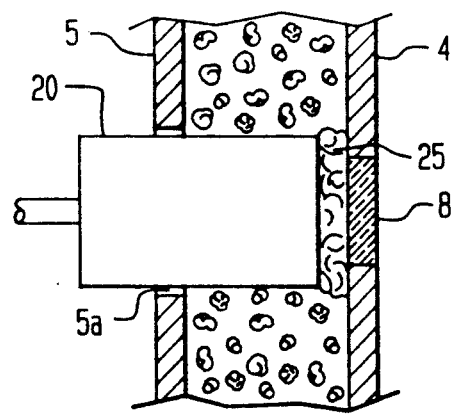
FIG. 2 is a view of the ram of FIG. 1 in its extended position.

The length of the assembly 15 must be sufficient to permit ram 20 essentially to traverse the distance between walls 4 and 5, so as to push a small mass of cotton 25 against window 8 when fully extended, as illustrated in FIG. 2.

Ram 20, which may constructed from a hollow metal cylinder, has a length about the same as that as the distance between walls 4 and 5. This assures that at least a part of the ram still is lodged in opening 5a even when fully extended. In this manner, no cotton will be trapped behind the ram during its retraction stroke. In addition, by maintaining a least a part of the ram within opening 5a during the entire operation, support continuously is provided for the ram.

Hydraulics or pneumatics may be employed to activate assembly 15, pneumatics being preferred. In most instances, pneumatic pressures of about 75 to 150 psi are suitable for sufficiently compressing the cotton so as to provide a cotton face of uniform density at window 8. Under such pressure, the face of the cotton mass typically will experience a pressure of about 10 psi; and the mass ordinarily will be compressed to a thickness of about 2 inches.

Conventional heavy duty, double-acting air cylinders capable of operating at 250 psi maximum are suitable for achieving such compression. Appropriate pneumatic hardware, including air control valves, solenoids, air supply, and related equipment will be obvious to those skilled in the art.

As to dimensions, a diameter of about 6-8 inches is suitable for ram 20 driven by a 1 ½-2 inch (diameter) pneumatic piston, whereby a small mass of cotton will be displaced and pressed against window 8, in comparison to the total volume of cotton travelling through chute 1.

During operation, each cotton mass being analyzed at window 8 is forced to pause a very brief time, typically less than 0.2 second, to be analyzed at window 8, before resuming its downward passage through holding chute 1. A substantial amount of the cotton passing through the chute, e.g., at least 30% is not displaced towards the analyzer, and passes through the chute without compression or analysis. In many instances, over 90% of the cotton will pass through the holding zone without analysis.

Off-the-shelf electronic time delay relays may be used to trigger the analyzing instruments to take readings only when compression of the cotton mass is at its maximum. For example, a relay with a timing range of 0.1 to 1.0 seconds may direct the compression cycle to start. The timer electrically may signal a directional solenoid air valve which further signals the pneumatic cylinder to activate. An electrical signal is sent to the computer by the relay about the same time as the piston is directed to extend to define the precise time for the computer to take a reading. Sufficient time is allowed for the piston to fully extend before the timer directs the cylinder to return. This time, typically 1 second, is used to delay the analyzer's computer from taking its reading until full extension occurs. If full extension of the piston is not achieved before the preset time delay occurs such as when the holding chute is fully filled with cotton, the piston remains partially extended for the full time to permit analysis before it retracts.

Figure 3:
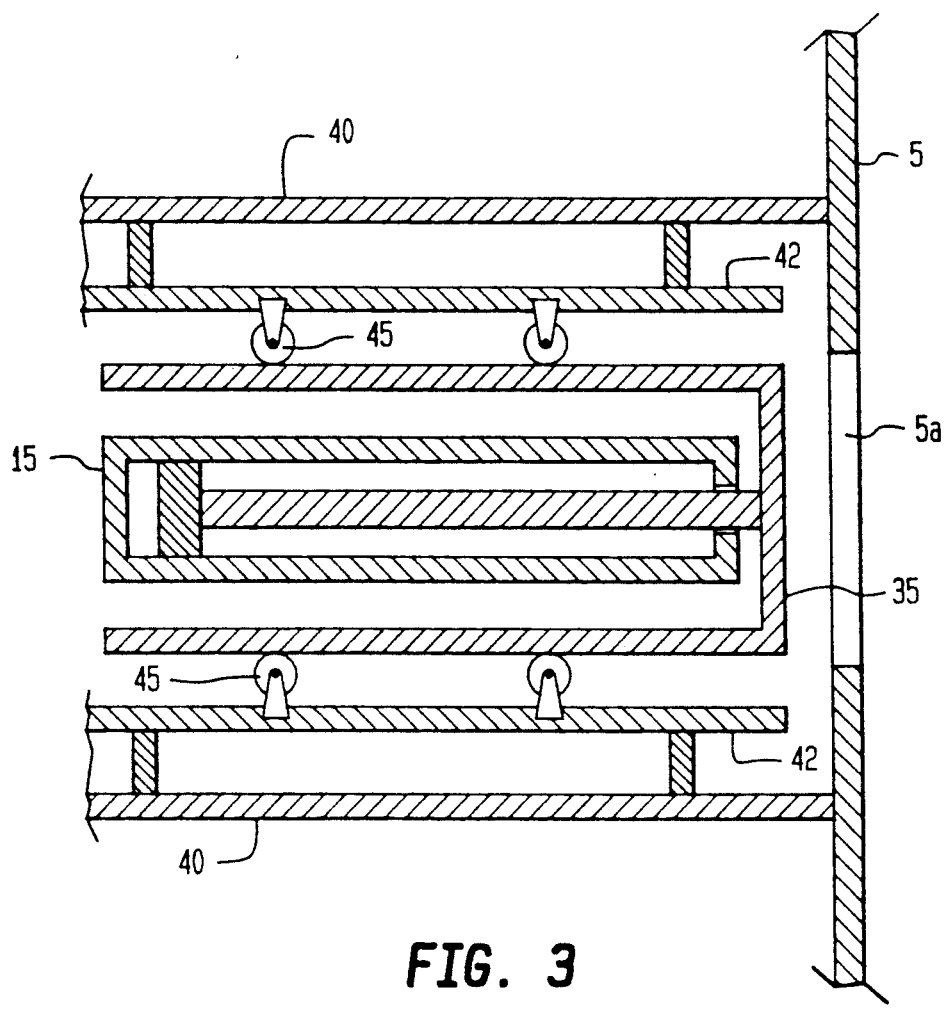
FIGS. 3–5 illustrate preferred embodiments of the compression device of FIG. 1.
Figure 4:
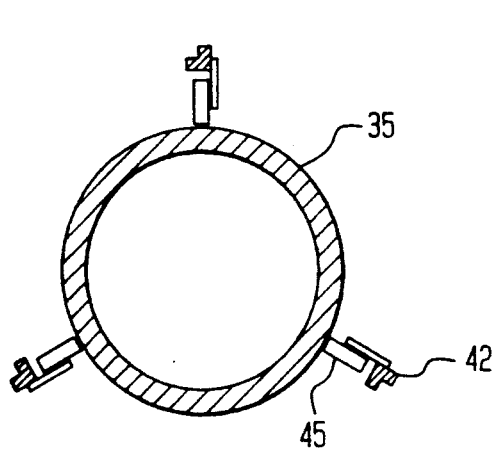

A preferred cotton compression means is illustrated in FIGS. 3 and 4. Referring thereto, the ram comprises a hollow, moveable cylinder 35. The piston rod of piston-cylinder assembly 15 is attached to the interior of the closed end of cylinder 35. In its retracted position, the piston-cylinder assembly is nested within or enveloped by hollow cylinder 35.

Surrounding the piston-cylinder assembly is a chamber defined by chamber walls 40 connected to chute wall 5. A plurality of elongated members 42, which are parallel to cylinder 35, are secured to the inside of the chamber. Multiple casters 45 are connected to members 42 adjacent to hollow cylinder 35, to guide the cylinder 35 on its compression and retraction strokes. Preferably, three casters are spaced around the cylinder, as shown in the FIG. 4, at two locations along the length of the cylinder, for a total of six casters.

By means of the features illustrated in FIGS. 3 and 4, overhang stress is minimized, the overall device is strengthened, and the piston rod of assembly 15 is protected.

Figure 5:
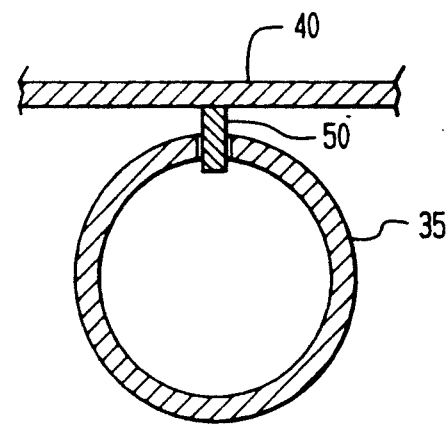

To further stabilize cylinder 35 and prevent it from rotating, a guide rod 50 may be secured to one of the chamber walls 40 to ride in a slot in cylinder 35, as shown in FIG. 5.

In addition to analyzing for trash or moisture, the present invention may be employed to determine the diameter of cotton fibers, entanglement of fibers (neps), relative maturities of fibers, different kinds of impurities such as plant parts or soil particles, as well as dimensions of impurities.

Other types of analyzers, which do not require a window or lens in the wall surface, may be employed in the present invention. For example, that part of the wall surface on which the cotton mass is compressed may include electrode sensors that detect moisture.

In view of the fact that the piston-cylinder-ram assembly of the present invention provides a mass of cotton having essentially the same density each time a mass is compressed against wall 4, some forms of analysis may be performed elsewhere than at the point of compression, whereby the mass, while being maintained under pressure, may be extracted from the initial point of compression by, for example, robotics, to be analyzed elsewhere. In this embodiment, the piston-cylinder-ram assembly functions to form a sample for remote analysis.

With further regard to this latter embodiment, if the amount of cotton passing through the holding chute is maintained at a substantially constant value, then the mass of cotton pressed against wall 4 on each cycle will be substantially the same quantity each time. Since some forms of cotton analysis require only a constant amount of material, rather than a face of uniform density, in these instances it will be unnecessary to maintain the sample under pressure during removal and transfer to the remote analyzer.

In the case of analyzing other flowable solids such as flowable particulate material (as opposed to pieces of bulk cotton), the material may be permitted to flow downwardly through the zone or chute by gravity; or it may flow horizontally through the zone by means of fluid entrainment or pressure differential.

We claim:

1. Apparatus for analyzing flowable solids comprising
   a. means to move said flowable solids through a zone partly defined by two immovable opposing surfaces, in a pathway generally parallel to said surfaces;
   b. means connected to said zone to intermittently displace part of said flowable solids moving through said zone from said pathway toward a first of said two surfaces, away from the second of said surfaces, while, during displacement, permitting part of said flowable solids moving through said zone to pass said displacement means without being displaced; wherein said displacement means includes means to press said displaced part of said flowable solids against said first surface;
   c. analyzing means adjacent said first surface whereat said flowable solids are pressed, to analyze said pressed flowable solids; and
   d. means to remove pressure from said pressed flowable solids after analysis thereof, and to permit said pressed flowable solids to resume said pathway through said zone.

2. The apparatus of claim 1 wherein said displacing and pressing means comprises a ram which extends into said zone through an opening in said second surface; wherein the length of said ram is such that at least part of said ram is lodged in said opening when said ram is fully extended into said zone.

3. The apparatus of claim 2 further including a piston-cylinder assembly having a piston rod that is connected to said ram.

4. Apparatus for analyzing flowable solids comprising
   a. means to move said flowable solids through a zone partly defined by two stationary opposing surfaces, in a pathway generally parallel to said surfaces;
   b. means connected to said zone to intermittently displace part of said flowable solids moving through said zone from said pathway toward a first of said two surfaces, away from the second of said surfaces, while, during displacement, permitting part of said flowable solids moving through said zone to pass said displacement means without being displaced; wherein said displacement means includes means to press said displaced part of said flowable solids against said first surface;
   c. analyzing means adjacent said first surface whereat said flowable solids are pressed, to analyze said pressed flowable solids;
   d. means to remove pressure from said pressed flowable solids after analysis thereof and to permit said pressed flowable solids to resume said pathway through said zone;
   wherein said displacing and pressing means comprises a ram which extends into said zone through an opening in said second surface; wherein the length of said ram is such that at least part of said ram is lodged in said opening when said ram is fully extended into said zone;
   e. a piston-cylinder assembly having a piston rod that is connected to said ram;
   wherein said ram comprises a longitudinally-moveable hollow cylinder; wherein said piston-cylinder assembly, in its retracted position, is nested within said moveable hollow cylinder.

5. Apparatus for analyzing cotton comprising
   a. means to move cotton through a zone partly defined by two immovable opposing surfaces, in a pathway generally parallel to said surfaces;
   b. means connected to said zone to displace a mass of said cotton from said pathway toward a first of said two surfaces, away from the second of said surfaces, while, during displacement, permitting part of the cotton moving through said zone to pass said displacement means without being displaced; wherein said displacement means includes means to press said mass against said first surface so that said mass may be analyzed.

6. The apparatus of claim 5 wherein said displacing and pressing means comprises means to intermittently displace and press cotton against said first surface at time intervals.

7. The apparatus of claim 5 wherein said displacing and pressing means is sufficient to press said mass against said first surface to form a face of uniform cotton density on that part of said mass which is pressed against said first surface.

8. The apparatus of claim 7 further including cotton analyzing means adjacent said first surface whereat said mass is pressed, to analyze said face of said mass for a property selected from the group consisting of color, trash content, moisture content, and combinations thereof.

9. The apparatus of claim 8 wherein said displacing and pressing means comprises pneumatic means.

10. The apparatus of claim 9 wherein said pneumatic means comprises
    a. a piston-cylinder assembly including a piston rod;
    b. a ram connected to said piston rod; and
    c. a hole in said second surface through which said ram and piston rod may pass and extend toward said first surface.

11. Apparatus for analyzing cotton comprising
    a. means to move cotton through a zone partly defined by two stationary opposing surfaces, in a pathway generally parallel to said surfaces;
    b. means connected to said zone to displace a mass of said cotton from said pathway toward a first of said two surfaces, away from the second of said surfaces, while, during displacement, permitting part of the cotton moving through the zone to pass said displacement means without being displaced; wherein said displacement means includes means to press said mass against said first surface so that said mass may be analyzed;

wherein said displacing and pressing means is sufficient to press said mass against said first surface to form a face of uniform cotton density on that part of said mass which is pressed against said first surface;

c. cotton analyzing means adjacent said first surface whereat said mass is pressed, to analyze said face of said mass for a property selected from the group consisting of color, trash content, moisture content, and combinations thereof;

wherein said displacing and pressing means comprises pneumatic means;

wherein said pneumatic means comprises
 i. a piston-cylinder assembly including a piston rod;
 ii. a ram connected to said piston rod; and
 iii. a hole in said second surface through which said ram and piston rod may pass and extend toward said first surface;

wherein said ram comprises a longitudinally-moveable hollow cylinder; wherein said piston-cylinder assembly, in its retracted position, is nested within said moveable hollow cylinder.

12. The apparatus of claim 7 wherein said displacing and pressing means comprises means to intermittently displace and press cotton against said first surface at time intervals.

13. The apparatus of claim 5 wherein said displacing and pressing means comprises a ram which extends into said zone through an opening in said second surface; wherein the length of said ram is such that a least part of said ram is lodged in said opening when said ram is fully extended into said zone.

14. The apparatus of claim 13, wherein said displacing and pressing means comprises means to intermittently displace and press cotton against said first surface at time intervals.

15. Apparatus for analyzing cotton comprising
a means to move bulk cotton through a zone partly defined by two immovable opposing surfaces, in a pathway generally parallel to said surfaces;
b. means connected to said zone to displace a mass of said cotton from said pathway toward a first of said two surfaces, away from the second of said surfaces, and to press said mass against said first surface with sufficient force so that said mass presents a face of uniform cotton density on that part of said mass which is pressed against said first surface; and
c. analyzing means adjacent said first surface whereat said mass is pressed, to analyze said mass for a property selected from the group consisting of color, trash content, moisture content, and combinations thereof.

16. The apparatus of claim 15 wherein said displacing and pressing means comprises means to intermittently press cotton against said first surface at time intervals.

17. The apparatus of claim 16 wherein said displacing and pressing means comprises pneumatic means.

18. The apparatus of claim 17 wherein said pneumatic means comprises
a. a piston-cylinder assembly including a piston rod;
b. a ram connected to said piston rod; and
c. a hole in said second surface through which said ram and piston rod may pass and extend toward said first surface.

19. The apparatus of claim 18 wherein said ram comprises a longitudinally-moveable hollow cylinder; wherein said piston-cylinder assembly, in its retracted position, is nested within said moveable hollow cylinder.

20. The apparatus of claim 19 further including caster means adjacent said moveable hollow cylinder to guide said moveable hollow cylinder.

21. A process for analyzing bulk cotton that is moving through a zone defined by two immovable opposing surfaces, in a pathway generally parallel to said surfaces comprising displacing a mass of said cotton from said pathway toward a first of said two surfaces, away from the second of said surfaces, and pressing said mass against said first surface with sufficient force so that said mass presents a face of uniform cotton density on that part of said mass which is pressed against said first surface, so that said mass may be accurately analyzed for at least one of the following properties: color, trash content, moisture content, and combinations thereof.

22. The process of claim 21 further including analyzing said face for a property selected from the group consisting of color, trash content, moisture content, and combinations thereof.

23. The process of claim 22 wherein said displacing and pressing steps comprise intermittently displacing and pressing cotton against said first surface at time intervals.

24. The process of claim 21 wherein said displacing and pressing steps comprise intermittently displacing and pressing cotton against said first surface at time intervals.

25. Apparatus for analyzing cotton comprising
a. means to move cotton through a zone partly defined by two opposing surfaces in a pathway generally parallel to said surfaces;
b. pneumatic means connected to said zone to displace a mass of said cotton from said pathway toward a first of said two surfaces, away from the second of said surfaces, while permitting part of the cotton moving through said zone to pass therethrough without displacment; wherein said displacement means includes means to press said mass against said first surface with sufficient force so that said mass presents a face of uniform cotton density on that part of said mass which is pressed against said first surface; wherein said pneumatic means comprises:
 i. a piston-cylinder assembly including a piston rod;
 ii. a longitudinally-moveable hollow cylinder connected to said piston rod, wherein said piston-cylinder assembly, in its retracted position, is nested within said moveable hollow cylinder;
 iii. caster means adjacent said moveable hollow cylinder to guide said moveable hollow cylinder; and
 iv. a hole in said second surface through which said ram and piston may pass and extend toward said first surface;
c. cotton analyzing means adjacent said first surface whereat said mass is pressed, to analyze said face of said mass for a property selected from the group consisting of color, trash content, moisture and combinations thereof.

26. Apparatus for analyzing cotton comprising a. means to move bulk cotton through a zone partly defined by two opposing surfaces in a pathway generally parallel to said surfaces;
b. means connected to said zone to displace a mass of said cotton from said pathway toward a first of said two surfaces, away from the second of said surfaces, and to press said mass against said first surface with sufficient force so that said mass presents a face of uniform cotton density on that part of said mass which is pressed against said first surface; and
c. analyzing means adjacent said first surface whereat said mass is pressed, to analyze said mass for a property selected from the group consisting of color, trash content, moisture content, and combinations thereof.; wherein said analyzing means comprises:
  i. lens means in said first surface so that said mass is pressed against said lens means; and
  ii. optical analyzing means adjacent said lens means to determine color and trash level in said mass of cotton pressing against said lens.

27. The apparatus of claim 26 further including infrared analyzing means adjacent said lens means.

28. Apparatus for analyzing cotton comprising
a. means to move bulk cotton through a zone partly defined by two opposing surfaces in a pathway generally parallel to said surfaces;
b. pneumatic means connected to said zone to intermittently displace a mass of said cotton from said pathway toward a first of said two surfaces, away from the second of said surfaces, at time intervals, and to press said mass against said first surface with sufficient force so that said mass presents a face of uniform cotton density on that part of said mass which is pressed against said first surface; and
c. analyzing means adjacent said first surface whereat said mass is pressed, to analyze said mass for a property selected from the group consisting of color, trash content, moisture content, and combinations thereof.; wherein said analyzing means comprises:
  i. lens means in said first surface so that said mass is pressed against said lens means; and
  ii. optical analyzing means adjacent said lens means to determine color and trash level in said mass of cotton pressing against said lens.

29. The apparatus of claim 28 further including infrared analyzing means adjacent said lens means.

30. A process for analyzing bulk cotton that is moving through a zone defined by two opposing surfaces in a pathway generally parallel to said surfaces comprising intermittently displacing a mass of said cotton from said pathway toward a first of said two surfaces, away from the second of said surfaces, at time intervals, and pressing said mass against said first surface with sufficient force so that said mass presents a face of uniform cotton density on that part of said mass which is pressed against said first surface, so that said mass may be accurately analyzed for at least one of the following properties: color, trash content, moisture content, and combinations thereof; employing electromagnetic energy to analyze said face for a property selected from the group consisting of color, trash content, moisture content, and combinations thereof.

31. The process of claim 30 wherein said displacing and pressing steps comprise pneumatically compressing said mass against said first surface.

* * * * *